(12) United States Patent
Abedini

(10) Patent No.: US 8,801,316 B1
(45) Date of Patent: Aug. 12, 2014

(54) WATER JET TOOTHBRUSH ASSEMBLY

(71) Applicant: Reza Abedini, Portland, OR (US)

(72) Inventor: Reza Abedini, Portland, OR (US)

( * ) Notice: Subject to any disclaimer, the term of this patent is extended or adjusted under 35 U.S.C. 154(b) by 0 days.

(21) Appl. No.: 13/833,418

(22) Filed: Mar. 15, 2013

(51) Int. Cl.
*A46B 11/06* (2006.01)
*A46B 15/00* (2006.01)

(52) U.S. Cl.
CPC ........... *A46B 11/063* (2013.01); *A46B 15/0081* (2013.01)
USPC ................................. 401/289; 401/16; 401/18

(58) Field of Classification Search
USPC ........... 401/268, 270, 289, 290, 282, 291, 16, 401/36, 18
See application file for complete search history.

(56) References Cited

U.S. PATENT DOCUMENTS

| | | | | |
|---|---|---|---|---|
| 1,479,275 A | * | 1/1924 | Beil | 401/287 |
| 2,516,195 A | * | 7/1950 | Finton | 401/289 |
| 2,855,619 A | * | 10/1958 | Graham | 401/46 |
| 3,135,989 A | * | 6/1964 | Gatti | 401/289 |
| 3,593,707 A | * | 7/1971 | Pifer | 601/163 |
| 3,610,234 A | | 10/1971 | Oates | |
| 4,175,879 A | | 11/1979 | Molinari | |
| 4,257,433 A | | 3/1981 | Kwan | |
| 5,297,884 A | * | 3/1994 | Cubillas | 401/268 |
| 6,047,429 A | | 4/2000 | Wu | |
| D648,941 S | | 11/2011 | Leung | |
| 2004/0045107 A1 | | 3/2004 | Egeresi | |
| 2011/0262879 A1 | | 10/2011 | Hegemann | |
| 2012/0225404 A1 | | 9/2012 | Kamkar et al. | |

\* cited by examiner

*Primary Examiner* — David Walczak

(57) ABSTRACT

A water jet toothbrush assembly injects water into a user's mouth to remove plaque and debris. The assembly includes an elongated member having a head and a handle. The head has a plurality of apertures positioned therein. A conduit extends through an interior space of the elongated member. A first end of the conduit is in fluid communication with a hose when the hose is coupled to the handle. A second end of the conduit is positioned proximate the apertures wherein the conduit is configured for delivering water to the apertures. A channel extends through an interior space of a cleaning attachment. A first end of the channel is in fluid communication with the hose when the hose is coupled to the cleaning attachment. A second end of the channel is aligned with a hole of the cleaning attachment wherein the channel is configured for delivering water to the hole.

10 Claims, 4 Drawing Sheets

WATER JET TOOTHBRUSH ASSEMBLY

BACKGROUND OF THE DISCLOSURE

Field of the Disclosure

The disclosure relates to toothbrush assemblies and more particularly pertains to a new toothbrush assembly for rinsing and cleaning a user's mouth by injecting a stream of water to remove plaque and food debris between teeth and below the gumline.

SUMMARY OF THE DISCLOSURE

An embodiment of the disclosure meets the needs presented above by generally comprising an elongated member having a head coupled to a handle. The head has a plurality of apertures positioned therein. A conduit extends through an interior space of the elongated member. A first end of the conduit is in fluid communication with a hose when the hose is coupled to the handle. A second end of the conduit is positioned proximate the apertures wherein the conduit is configured for delivering water to the apertures. A channel extends through an interior space of a cleaning attachment. A first end of the channel is in fluid communication with the hose when the hose is coupled to the cleaning attachment. A second end of the channel is aligned with a hole of the cleaning attachment wherein the channel is configured for delivering water to the hole.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
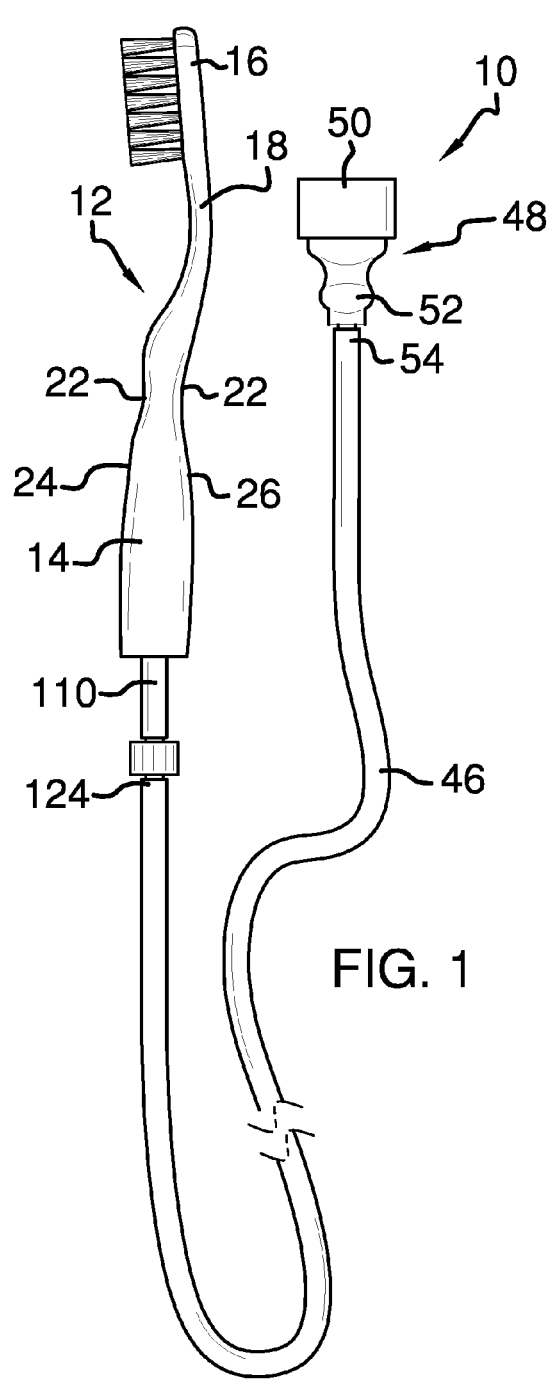
FIG. 1 is a side view of a water jet toothbrush assembly according to an embodiment of the disclosure.
Figure 2:
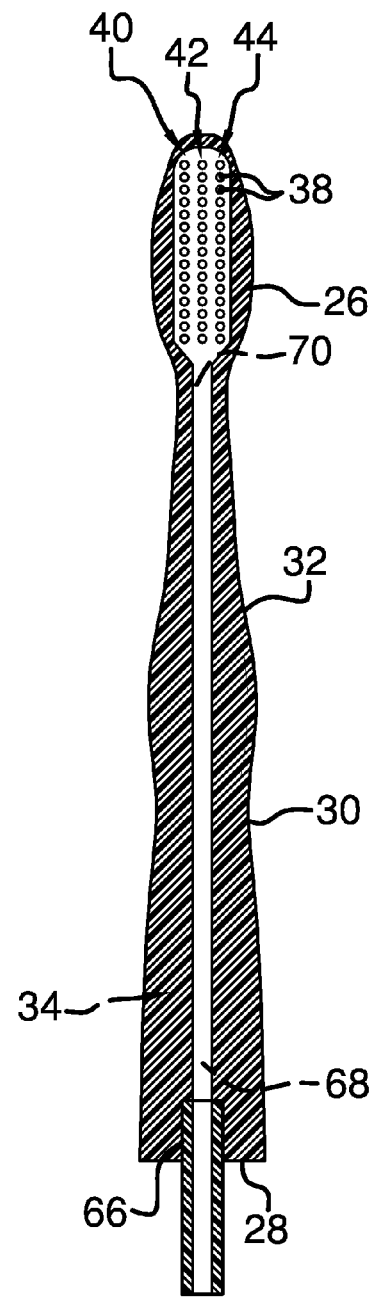
FIG. 2 is a back view of an embodiment of the disclosure.
Figure 3:
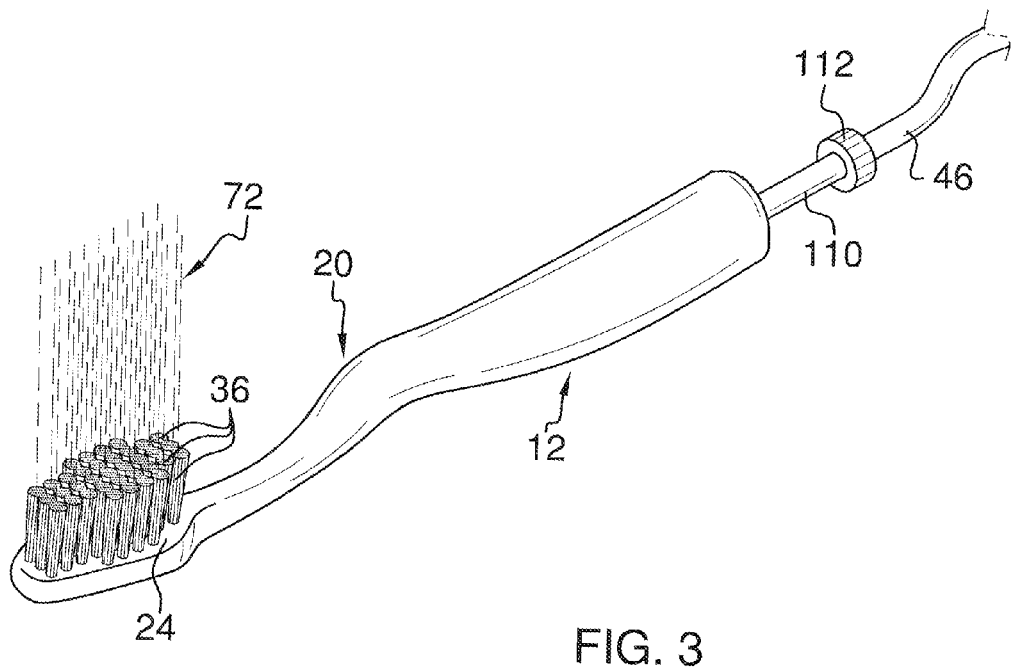
FIG. 3 is a top front side perspective view of an embodiment of the disclosure.
Figure 4:
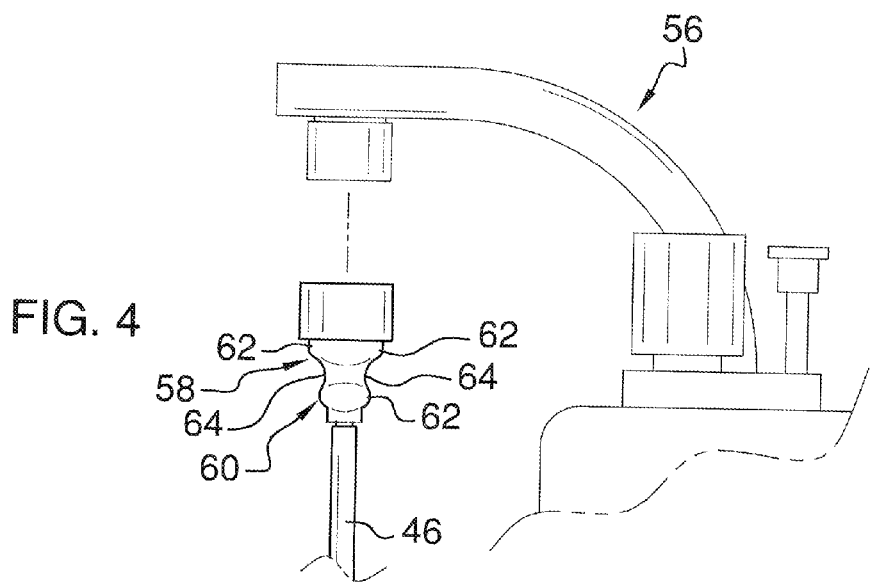
FIG. 4 is a side view of an embodiment of the disclosure in use.
Figure 5:
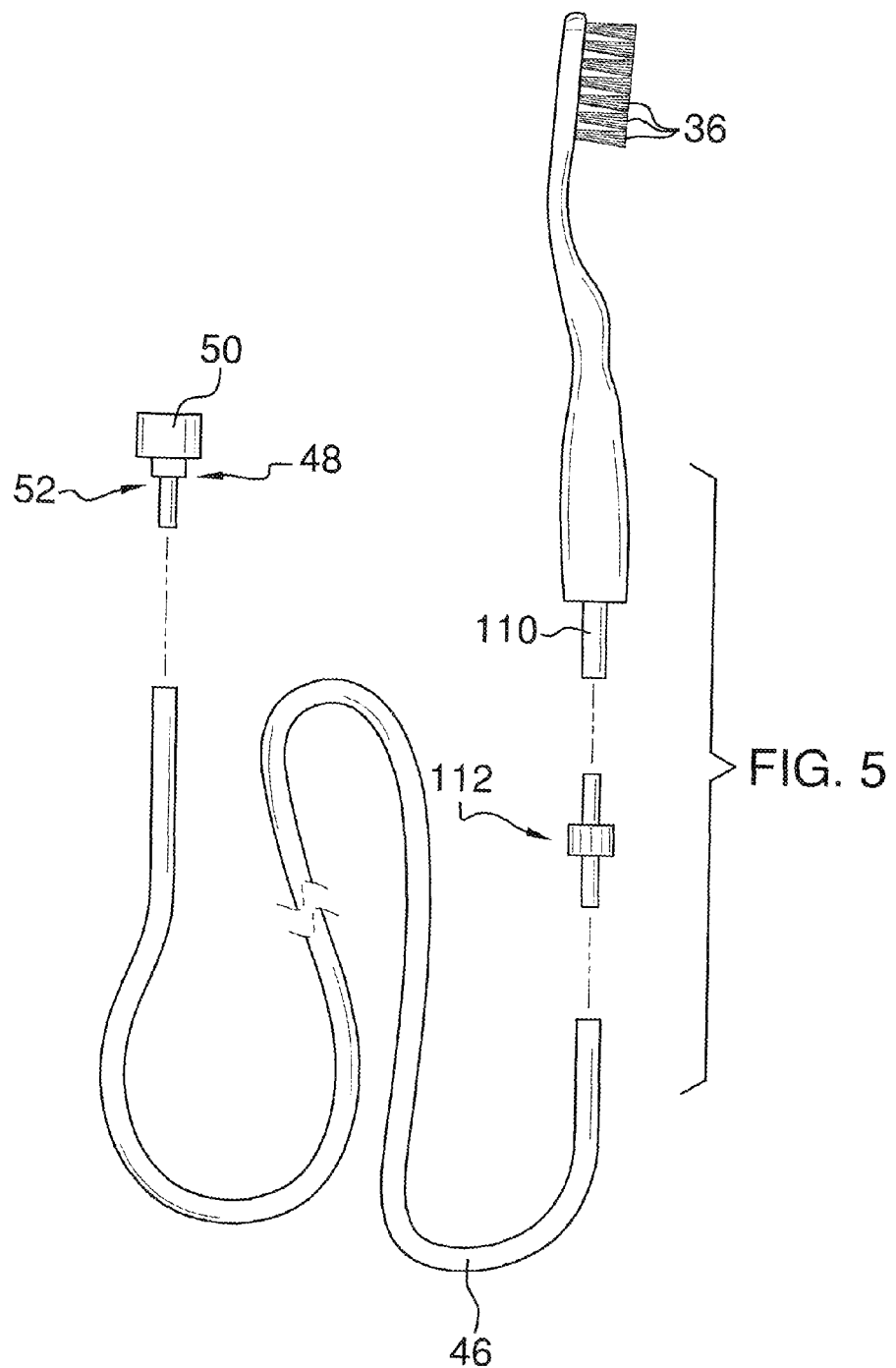
FIG. 5 is an exploded side view of an embodiment of the disclosure.
Figure 6:
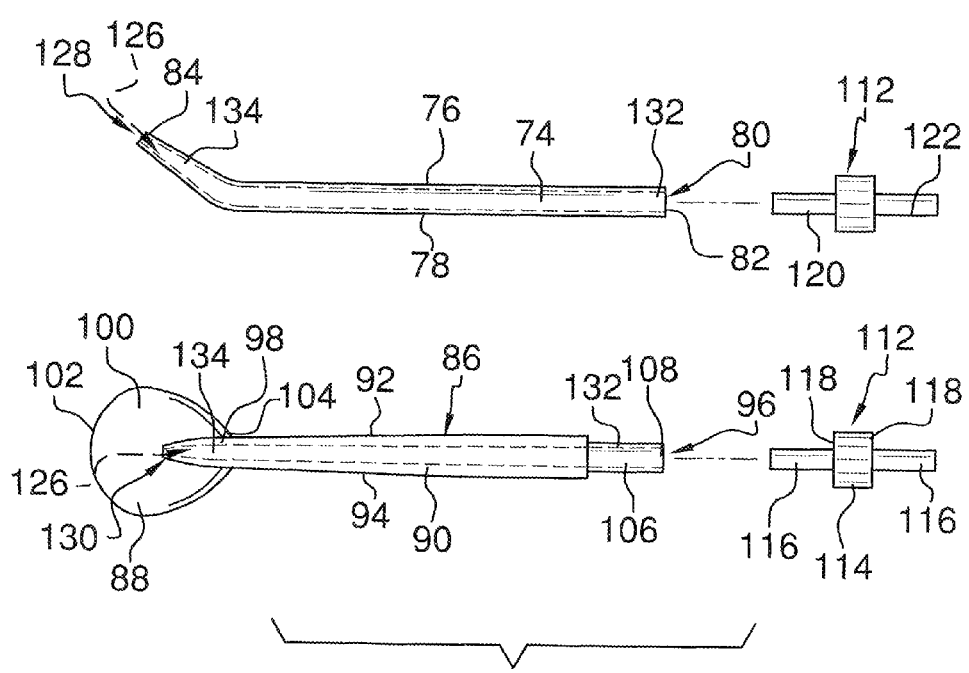
FIG. 6 is a side view of a cleaning attachment and a tongue scraper of an embodiment of the disclosure.

With reference now to the drawings, and in particular to FIGS. 1 through 6 thereof, a new water jet assembly embodying the principles and concepts of an embodiment of the disclosure and generally designated by the reference numeral 10 will be described.

As best illustrated in FIGS. 1 through 6, the water jet toothbrush assembly 10 generally comprises an elongated member 12 having a handle 14, a head 16, and a neck 18. The neck 18 is positioned between the head 16 and the handle 14 and is curved downwardly relative to the head 16. The head 16 is positioned transversely relative to the handle 14 and is substantially oval-shaped. A medial portion 20 of the elongated member 12 has a pair of annular depressions 22 positioned proximate the neck 18. Each of the depressions 22 is positioned on a respective one of a top side 24 and a bottom side 26 of the elongated member 12. The elongated member 12 tapers from a bottom end 28 of the handle 14 to a first end 30 of the depressions 22 and further tapers from a second end 32 of the depressions 22 to the head 16. An interior space 34 of the elongated member 12 is defined by the top side 24 and the bottom side 26 of the elongated member 12.

A plurality of bristles 36 is coupled to and extends outwardly from the head 16. The bristles 36 are coupled to the top side 24 of the head 16. A plurality of apertures 38 is positioned in the head 16. The apertures 38 comprise a first aperture array 40, a second aperture array 42, and a third aperture array 44. The apertures 38 of the first aperture array 40 are spaced and vertically aligned. The apertures 38 of the second aperture array 42 are spaced and vertically aligned. The apertures 38 of the third aperture array 44 are spaced and vertically aligned. The first aperture array 40 is spaced and horizontally aligned relative to the second and third aperture arrays 42, 44.

A hose 46 is couplable to the handle 14. A user may cut the hose 46 to a desirable length. A faucet coupler 48 has an upper portion 50 and a lower portion 52. The lower portion 52 is coupled to the hose 46. The upper portion 50 is adapted to couple a first end 54 of the hose 46 to a water source 56. The lower portion 52 has a first and second set 58, 60 of opposed convex arcuate portions 62. The lower portion 52 has a pair of opposed concave arcuate portions 64 extending between the first and second sets 58, 60 of opposed convex arcuate portions 62. A conduit 66 is positioned in and extends longitudinally through the interior space 34 of the elongated member 12. The conduit 66 has a first end 68 positioned opposite a second end 70. The first end 68 of the conduit 66 is in fluid communication with the hose 46 when the hose 46 is coupled to the handle 14. The second end 70 of the conduit 66 is positioned proximate the apertures 38 wherein the conduit 66 is configured for delivering water 72 from the hose 46 to the apertures 38. Thus, water 72 is delivered through the hose 46 using force and no electrical power is required.

A cleaning attachment 74 is couplable to the hose 46. The cleaning attachment 74 has an upper surface 76 and a lower surface 78 defining an interior space 80 of the cleaning attachment 74. The cleaning attachment 74 has an open first end 82 and an open second end 84. Alternatively, a tongue scraper 86 may be coupled to the hose 46. The tongue scraper 86 has a main surface 88 coupled to a graspable portion 90. The graspable portion 90 comprises an upper side 92 and a lower side 94 wherein the upper side 92 and the lower side 94 define an interior space 96 of the tongue scraper 86. A first end 98 of the graspable portion 90 is coupled to a bottom side 100 of the main surface 88. The main surface 88 has an arcuate first side 102 positioned opposite an arcuate second side 104. The graspable portion 90 is coupled to the arcuate second side 104 and extends outwardly therefrom. The main surface 88 of the tongue scraper 86 is rubbed against a tongue of the user so as to clean the surface of the user's tongue.

An extension 106 projects outwardly from the graspable portion 90. The extension 106 is coupled to a second end 108 of the graspable portion 90. A protrusion 110 extends outwardly from the bottom end 28 of the handle 14. A connector 112 has a ring 114 and a pair of projections 116 coupled to and extending outwardly from opposite ends 118 of the ring 114. A first one 120 of the projections 116 is insertable into a selectable one of the protrusion 110 of the handle 14, the extension 106 of the tongue scraper 86, and the open second end 84 of the cleaning attachment 74. In this manner, a user has the option of using the elongated member 12, the tongue scraper 86, or the cleaning attachment 74 depending on the user's particular cleaning needs. A user who attaches the elongated member 12 to the hose 46 is able to inject a stream of water 72 into the user's mouth while brushing. A second one 122 of the projections 116 is selectively insertable into a second end 124 of the hose 46.

A pair of channels 126 is provided. A first channel 128 is positioned in and extends longitudinally through the interior space 80 of the cleaning attachment 74. A second channel 130 is positioned in and extends though the interior space 96 of the tongue scraper 86. Each of the channels 126 has a first end 132 positioned opposite a second end 134. The first end 132 of the channels 126 is in fluid communication with the hose 46 when the hose 46 is coupled to a selectable one of the cleaning attachment 74 and the tongue scraper 86. The second end 134 of the first channel 128 is aligned with the open second end 84 of the cleaning attachment 74 wherein the first channel 128 is configured for delivering water 72 from the hose 46 out through the open second end 84. In this manner, a user who attaches either the cleaning attachment 74 or the tongue scraper 86 to the hose 46 is able to inject a stream of water 72 into the user's mouth without simultaneously brushing.

In use, as stated above and shown in the Figures, a user attaches the faucet coupler 48 to the hose 46 and the water source 56, such as a faucet. Based on the user's preference, the hose 46 is attached to the elongated member 12, the cleaning attachment 74, or the tongue scraper 86. The water source 56 is then turned on and the water 72 flows through an associated one of the channels 126 or the conduit 66. Attaching the hose 46 to the elongated member 12 injects a stream of water 72 into the user's mouth while brushing. Attaching the hose 46 to the cleaning attachment 74 or the tongue scraper 86 injects a stream of water 72 into the user's mouth when the user is not brushing. The water 72 is designed to clean the entire mouth of the user, including between the user's teeth and below the gumline. The tongue scraper 86 can be rubbed against a surface of a user's tongue so as to clean the user's tongue.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:
1. A water jet toothbrush assembly comprising:
an elongated member having a head coupled to a handle;
an interior space extending through said elongated member, said interior space being defined by a top side and a bottom side of said elongated member;
a plurality of bristles coupled to and extending outwardly from said head;
a plurality of apertures positioned in said head;
a hose couplable to said handle;
a conduit positioned in and extending longitudinally through said interior space of said elongated member, said conduit having a first end positioned opposite a second end, said first end of said conduit being in fluid communication with said hose when said hose is coupled to said handle, said second end of said conduit being positioned proximate said apertures wherein said conduit is configured for delivering water from said hose to said apertures;
a cleaning attachment couplable to said hose, said cleaning attachment having an upper surface and a lower surface defining an interior space of said cleaning attachment, said cleaning attachment having a hole positioned in a first end of said cleaning attachment;
a first channel positioned in and extending longitudinally through said interior space of said cleaning attachment, said first channel having a first end positioned opposite a second end, said first end of said first channel being in fluid communication with said hose when said hose is coupled to said cleaning attachment, said second end of said first channel being aligned with said hole of said cleaning attachment wherein said first channel is configured for delivering water from said hose to said hole;
a tongue scraper couplable to said hose, said tongue scraper having a main surface coupled to a graspable portion, said graspable portion comprising an upper side and a lower side wherein said upper side and said lower side define an interior space of said tongue scraper;
an extension projecting outwardly from said graspable portion, said extension being coupled to a second end of said graspable portion;
a protrusion extending outwardly from a bottom end of said handle; and
a connector having a ring and a pair of projections coupled to and extending outwardly from opposite ends of said ring;
wherein a first one of said projections is insertable into a selectable one of said protrusion of said handle, said extension of said tongue scraper, and an open second end of said cleaning attachment; and
wherein a second one of said projections is selectively insertable into a second end of said hose.
2. The assembly of claim 1, further comprising:
a plurality of apertures positioned in said head, said apertures comprising a first aperture array, a second aperture array, and a third aperture array;
wherein said apertures of said first aperture array are spaced and vertically aligned, said apertures of said second aperture array are spaced and vertically aligned, and said apertures of said third aperture array are spaced and vertically aligned; and wherein said first aperture array is spaced and horizontally aligned relative to said second and third aperture arrays.

3. The assembly of claim 1, further comprising a faucet coupler having an upper portion and a lower portion wherein said lower portion is coupled to said hose and said upper portion is adapted to couple a first end of said hose to a water source.

4. The assembly of claim 3, further comprising said lower portion of said faucet coupler having a first and second set of opposed convex arcuate portions and a pair of opposed concave arcuate portions extending between said first and second sets of opposed convex arcuate portions.

5. The assembly of claim 1, further comprising:
said elongated member having a neck, said neck being positioned between said head and said handle; and
a medial portion of said elongated member having a pair of annular depressions positioned proximate said neck, each of said depressions being positioned on a respective one of a top side and a bottom side of said elongated member.

6. The assembly of claim 5, further comprising said elongated member tapering from a bottom end of said handle to a first end of said depressions and further tapering from a second end of said depressions to said head.

7. The assembly of claim 5, further comprising said neck being curved downwardly relative to said head.

8. The assembly of claim 1, further comprising said main surface having an arcuate first side positioned opposite an arcuate second side, said graspable portion being coupled to said arcuate second side and extending outwardly therefrom.

9. The assembly of claim 1, further comprising a second channel positioned in and extending through said interior space of said tongue scraper, said second channel having a first end positioned opposite a second end, said first end of said second channel being in fluid communication with said hose when said hose is coupled to said tongue scraper.

10. A water jet toothbrush assembly comprising:
an elongated member having a handle, a head, and a neck, said neck being positioned between said head and said handle, said neck being curved downwardly relative to said head, said head being positioned transversely relative to said handle, said head being substantially oval-shaped, a medial portion of said elongated member having a pair of annular depressions positioned proximate said neck, each of said depressions being positioned on a respective one of a top side and a bottom side of said elongated member, said elongated member tapering from a bottom end of said handle to a first end of said depressions and further tapering from a second end of said depressions to said head;
an interior space extending through said elongated member, said interior space of said elongated member being defined by said top side and said bottom side of said elongated member;
a plurality of bristles coupled to and extending outwardly from said head, said bristles being coupled to said top side of said head;
a plurality of apertures positioned in said head, said apertures comprising a first aperture array, a second aperture array, and a third aperture array, said apertures of said first aperture array being spaced and vertically aligned, said apertures of said second aperture array being spaced and vertically aligned, said apertures of said third aperture array being spaced and vertically aligned, said first aperture array being spaced and horizontally aligned relative to said second and third aperture arrays;
a hose couplable to said handle;
a faucet coupler having an upper portion and a lower portion, said lower portion being coupled to said hose, said upper portion being adapted to couple a first end of said hose to a water source, said lower portion having a first and second set of opposed convex arcuate portions, said lower portion having a pair of opposed concave arcuate portions extending between said first and second sets of opposed convex arcuate portions;
a conduit positioned in and extending longitudinally through said interior space of said elongated member, said conduit having a first end positioned opposite a second end, said first end of said conduit being in fluid communication with said hose when said hose is coupled to said handle, said second end of said conduit being positioned proximate said apertures wherein said conduit is configured for delivering water from said hose to said apertures;
a cleaning attachment couplable to said hose, said cleaning attachment having an upper surface and a lower surface defining an interior space of said cleaning attachment, said cleaning attachment having an open first end and an open second end;
a tongue scraper couplable to said hose, said tongue scraper having a main surface coupled to a graspable portion, said graspable portion comprising an upper side and a lower side wherein said upper side and said lower side define an interior space of said tongue scraper, a first end of said graspable portion being coupled to a bottom side of said main surface, said main surface having an arcuate first side positioned opposite an arcuate second side, said graspable portion being coupled to said arcuate second side and extending outwardly therefrom;
an extension projecting outwardly from said graspable portion, said extension being coupled to a second end of said graspable portion;
a protrusion extending outwardly from said bottom end of said handle;
a connector having a ring and a pair of projections coupled to and extending outwardly from opposite ends of said ring, a first one of said projections being insertable into a selectable one of said protrusion of said handle, said extension of said tongue scraper, and said open second end of said cleaning attachment, a second one of said projections being selectively insertable into a second end of said hose;
a first channel positioned in and extending longitudinally through said interior space of said cleaning attachment;
a second channel positioned in and extending though said interior space of said tongue scraper;
wherein each of said channels has a first end positioned opposite a second end, said first end of said channels being in fluid communication with said hose when said hose is selectively coupled to an associated one of said cleaning attachment and said tongue scraper; and
wherein said second end of said first channel is aligned with said open second end of said cleaning attachment wherein said second channel is configured for delivering water from said hose out through said open second end.

* * * * *